United States Patent [19]
Amis

[11] Patent Number: 5,575,819
[45] Date of Patent: Nov. 19, 1996

[54] ARTIFICIAL LIGAMENTS

[75] Inventor: Andrew Amis, London, United Kingdom

[73] Assignee: Imperial College of Science and Technology, London, England

[21] Appl. No.: 348,199

[22] Filed: Nov. 28, 1994

Related U.S. Application Data

[63] Continuation of Ser. No. 827,479, Jan. 29, 1992, abandoned, which is a continuation of Ser. No. 474,678, Feb. 6, 1990, abandoned, which is a division of Ser. No. 97,861, Sep. 17, 1987, abandoned.

[30] Foreign Application Priority Data

Sep. 19, 1986 [GB] United Kingdom ............... 8622563

[51] Int. Cl.$^6$ .................................................. A61F 2/08
[52] U.S. Cl. ............................................................ 623/13
[58] Field of Search .................... 623/16, 13; 128/92 Y, 128/92 YY, 92 YV, 92 YT, 92 YQ, 92 YG, 92 YE; 606/228

[56] References Cited

U.S. PATENT DOCUMENTS

| | | | |
|---|---|---|---|
| 3,613,120 | 10/1971 | McFarland | 623/13 |
| 4,388,921 | 6/1983 | Sutter et al. | 623/16 X |
| 4,642,119 | 2/1987 | Shah | 623/13 |
| 4,662,886 | 5/1987 | Moorse et al. | 623/13 |
| 4,728,329 | 3/1988 | Mansat | 623/13 |
| 4,744,793 | 5/1988 | Parr et al. | 623/16 X |
| 4,773,910 | 9/1988 | Chen et al. | 623/13 |
| 4,776,851 | 10/1988 | Bruchman et al. | 623/13 |
| 4,778,468 | 10/1988 | Hunt et al. | 623/16 |
| 4,792,336 | 12/1988 | Hlavacek et al. | 623/13 |

FOREIGN PATENT DOCUMENTS

| | | | |
|---|---|---|---|
| 0106501 | 4/1984 | European Pat. Off. | 623/13 |
| 2747568 | 4/1979 | Germany | 623/13 |
| 3742695 | 6/1989 | Germany | 623/13 |

OTHER PUBLICATIONS

"The Gore-Tex™ Expanded Polytetrafluoroethylene Prosthetic Ligament", by C. William Bolton and William C. Bruchman, Clinical Orthopedics and Related Research, 196, Jun., 1985, pp. 202–213.

*Primary Examiner*—David H. Willse
*Attorney, Agent, or Firm*—Barnes & Thornburg

[57] ABSTRACT

An artificial ligament for connecting across a skeletal joint comprises a bundle of fibers 1 each comprising a plurality of filaments 1a of polyethylene terephthalate. The ligament is constructed by winding a plurality of turns of the fiber 1 onto a winding apparatus and then binding the ends to form loops 4.

Also disclosed is a ligament fixation device in the form of a cylindrical grommet, and a tensioning instrument for use in implanting an artificial ligament.

5 Claims, 4 Drawing Sheets

ARTIFICIAL LIGAMENTS

This is a continuation of application Ser. No. 07/827,479, filed Jan. 29, 1992, now abandoned, which is a continuation of Ser. No. 07/474,678, filed Feb. 6, 1990, now abandoned, which is a division of Ser. No. 07/097,861, filed Sep. 17, 1987, now abandoned.

The present invention relates to an artificial ligament which may be used to replace damaged or missing ligaments, particularly the anterior cruciate ligament (ACL) of the human knee joint, although similar artificial ligaments could be used at other sites, such as an ankle or in other species, for example the canine ACL.

Ligaments are found at all of the joints of the skeleton. They act to limit the motion of bones relative to each other, thus providing stability to the joint. Ligaments are effectively passive tensile restraints, which originate from one bone and insert, across the joint, on another. Artificial ligaments are required because the natural ligaments heal slowly and are often damaged irreparably.

When implanting an artificial ligament, although it is initially fixed in place by some type of fixation device, further fixation after surgery may be achieved by ingrowth of tissue into the ligament structure. Various types of ligament have been developed, of which an example is described in European Patent Publication No 106501. This particular ligament consists of multiple loops of a single continuous fibre of expanded polytetrafluoroethylene (PTFE), the fibre itself comprising solid nodes of PTFE extending across the fibre diameter and connected longitudinally by a number of fine fibrils. This structure creates porosity which allows tissue ingrowth, but it has been found that such tissue ingrowth is much more effective when it is continuous and uninterrupted. The fibril and node structure of this ligament prevents continuous tissue ingrowth.

According to a first aspect of the present invention there is provided an artificial ligament for connecting across a skeletal joint, the ligament comprising a plurality of substantially parallel fibres of polymeric material and having a first end for accommodating fixation means whereby the ligament may be secured to a first bone of said joint, and a second end for accommodating fixation means whereby the ligament may be secured, across the joint, to a second bone of said joint, wherein the fibres each comprise a plurality of smaller diameter unconnected filaments.

Thus the structure of the ligament of the present invention provides a scaffold on which new continuous ligamentous tissue originating within the host may be laid down. Animal studies have shown that the material is capable of supporting such ingrowth. Tissue ingrowth is facilitated by the fact that the main part of the implant is kept as parallel unconnected fibres, whereas a twisted, plaited or braided construction would cause the gaps between the filaments to close under load, thus strangling any tissue ingrowth. The ligament of the present invention will eventually become a composite of polymeric fibres and natural collagenous tissue. The benefit of this is that the tissue could gradually take over the load-bearing function of the implant as the polymer fibres are degraded in use. The time scale of this is unknown as yet, but is likely to be of the order of a few years. The strength of the composite structure is likely to be higher than that of the artificial ligament alone after some months, when it has been augmented by tissue, but not yet degraded mechanically or chemically.

Preferably the ligament has a loop at each end formed by binding the fibres together.

Preferably the ligament is made of polyethylene terephthalate fibres known as "Terylene" (Trade Mark) or "Dacron" (Trade Mark).

Preferably the diameter of the filaments is in the range 5 to 25 microns.

Preferably the fibres each comprise 20 filaments of 15 microns diameter.

This small diameter is important because the host tissue is able to encapsulate each filament on a microscopic scale and maintain this capsule, whereas a large implant body might lead to undesirable tissue changes in use.

The filaments may be of clover leaf cross section, but preferably they are of circular cross section. The circular cross section is preferred because material is slowly degraded in-vivo, and for this reason the circular cross section is best as it minimises the surface area. Because of this gradual degradation, there is probably an optimum filament diameter—a very small filament would lose its strength rapidly.

According to the first aspect of the present invention there is further provided a method of constructing an artificial ligament, the method comprising winding onto a winding apparatus a plurality of turns of a fibre of a polymeric material, said fibre comprising a plurality of smaller diameter unconnected filaments, and removing the ligament so constructed from the winding apparatus.

Preferably, the method includes forming a loop at each end of the ligament by binding the fibres together. Preferably the winding apparatus is an electrically driven drum with a collapsable section whereby the ligament may be removed from the drum.

According to a second aspect of the present invention there is provided fixation means for fixing an artificial ligament to a bone, said fixation means comprising a substantially cylindrical grommet having an aperture therein for accommodating a bone screw and a radially extending flange at one end thereof against which an end of the ligament locates.

The flange is thus located at the end of the grommet which is, in use, furthest away from the bone.

Preferably the grommet includes a tapering portion at the end opposite the flanged end for expanding a loop in an end of the ligament, and a central portion between said two ends which is of larger diameter than that of the bone screw which it accommodates.

Preferably the flanged end of the grommet is countersunk to completely accommodate the head of the bone screw.

Preferably the flange has a flat undersurface.

Thus, in use, two such grommets will be used with two suitable bone screws, one bone screw and one grommet being used to fix one end of the ligament to for example the tibia, and the other bone screw and grommet being used to fix the opposite end of the ligament to, for example the femur, across the knee joint.

The grommet may be made of stainless steel, for use with stainless steel bone screws, or alternatively of titanium or cobalt chrome alloys for use with cobalt chrome bone screws. The grommet may equally successfully be made of polymer or composite material.

The grommet may have a smooth turned finish, but alternatively it incorporates a fine pitch buttress thread form or a series of circumferential grooves with a saw-tooth form on the outer surface of the central portion to increase interlocking of the grommet with the bone.

Preferably, the outer surface of the central portion of the grommet is porous.

The grommets may be supplied as accessories to conventional bone screws. The reason for this is the variation in the size of the bones. It is essential that anchorage screws of exactly the correct length are used—if they are too long, the tips will protrude from the far side of the bone, perhaps causing irritation, fraying, or puncturing of overlying tissue, whereas if they are too short the tip of the screw will not engage the far side of the bone tube, so the screw will topple sideways easily when loaded.

All orthopaedic units have graduated sets of bone screws, so the correct length will always be available without the need to hold a large stock of special devices, such as would be the ease if the grommet was an integral part of the bone screw.

Alternatively, the grommet may be an integral part of the bone screw, in which case a number of different bone screw lengths would have to be provided.

In use, a tapping hole is drilled into the femur, the upper portion of the hole being opened out to accommodate the grommet. The bone screw is passed through the grommet and the loop at one end of the ligament is passed over the screw and the grommet, the screw and grommet then being driven in to trap the loop against the bone. This procedure is repeated on the tibia to pull the ligament tight through the knee joint.

According to a third aspect of the present invention there is provided a tensioning instrument for use in the implantation of an artificial ligament, said instrument comprising a handle, a member for engaging an end of the ligament, and means to mark a bone to indicate the correct position for attachment of the ligament to the bone.

The member for engaging an end of the ligament may, in the case of a ligament with looped ends, be shaped as a capstan.

Alternatively, said ligament engaging member may, in the case of a ligament without looped ends comprise two plates which can be screwed together to secure the ligament end therebetween, one or both of the plates being serrated.

In either case, the means for marking the bone comprises one or more downwardly pointing spikes.

In the case where a capstan shape is employed, the ligament engaging member may include a central aperture therein for accommodating a drill bit.

Preferably, the instrument includes means to apply tension to the ligament.

Preferably the instrument also includes means to indicate quantitatively the degree of tension in the ligament.

Embodiments of the present invention will now be described by way of example only, with reference to the accompanying drawings in which:

FIG. 1b shows alternate grommet configurations;

Figure 1:
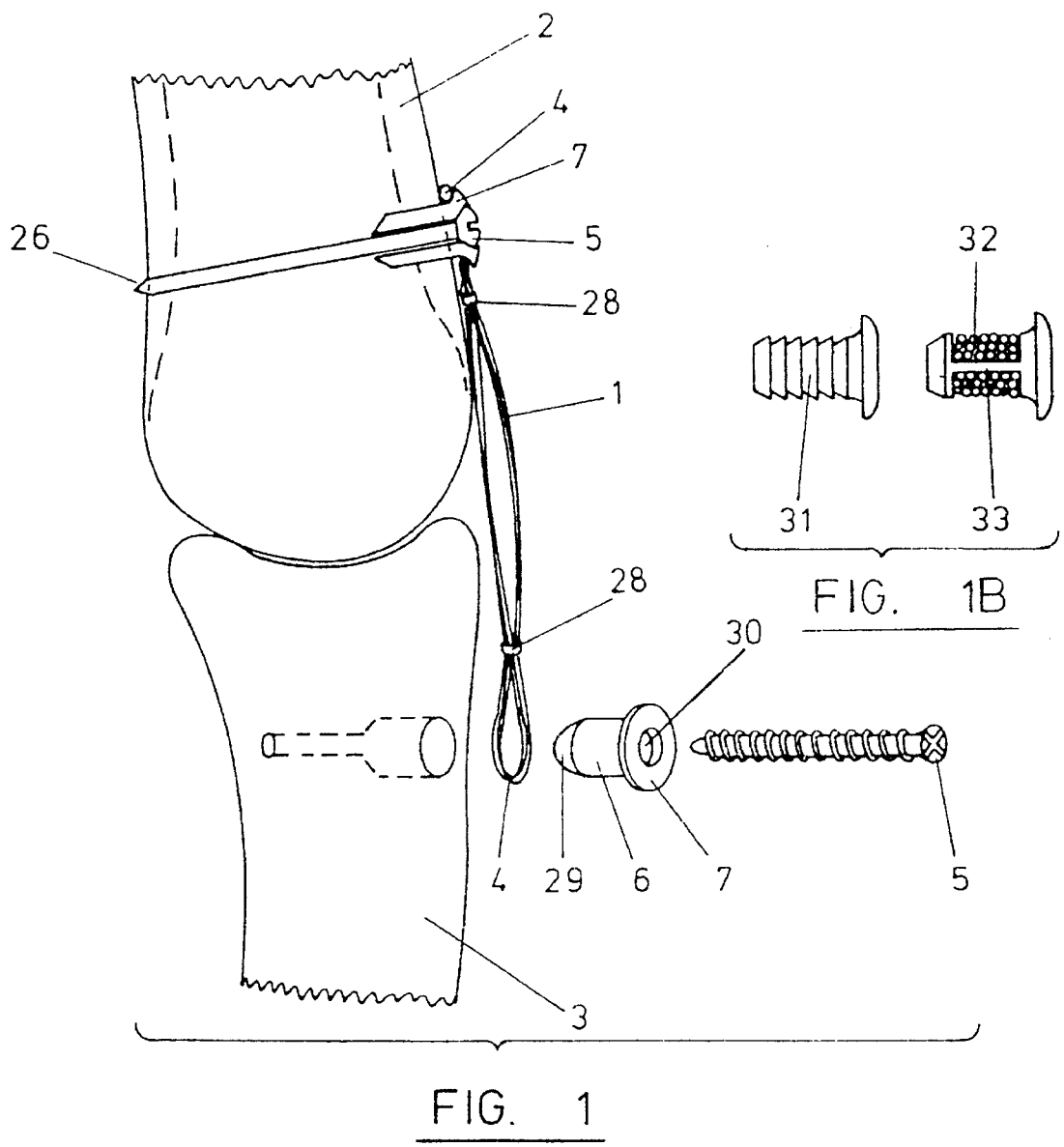
FIG. 1 is a schematic diagram of an artificial ligament and fixation means according to the present invention.
Figure 1A:
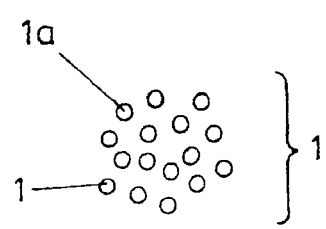
FIG. 1a is a cross section through a single fibre of the ligament.

Referring to FIGS. 1 and 1a an artificial ligament according to the present invention comprises a bundle of parallel fibres 1 of polyethylene terephthalate (PET), also known as "Terylene" (Trade Mark) or "Dacron" (Trade Mark). The type of PET chosen is the normal "bright" material which contains a low level of delustrent particles (normally titanium dioxide) which are used in most fabrics to give a matt appearance. The fibres are supplied on a bobbin as a yarn which is a bundle of filaments 1a twisted slightly together after spinning.

The filaments may have either circular or clover leaf cross sections, with diameters in the range 5 to 25 microns. Prototype implants have been made with a yarn of 20 filaments each 15 microns diameter.

When supplied by the manufacturer, the fibres are coated by traces of lubricants used during the spinnning. These are removed by washing with petroleum ether.

The ligament is constructed by winding multiple turns of the yarn on to an electrically driven drum, which has a counter attached. The drum circumference is chosen so that it equals twice the required implant length. The number of turns is chosen to give the required implant strength, which is determined from tests of cadaveric ligaments, data of forces expected in use, results of creep tests etc.

The implant is released from the drum after collapsing a segment of the drum surface towards the centre. It is then hung on a hook, with a weighted hook at the bottom end, then a loop 4 is formed by binding the implant at each end 28, using the same yarn material. This binding is only intended to keep the loops at each end for convenience during handling, so it is not extensive.

Thus the implant structure is effectively a collection of parallel fibres 1 of the yarn, each fibre containing multiple filaments 1a. It has a loop 4 at each end, the yarn being wound in a continuous length.

Figure 2:
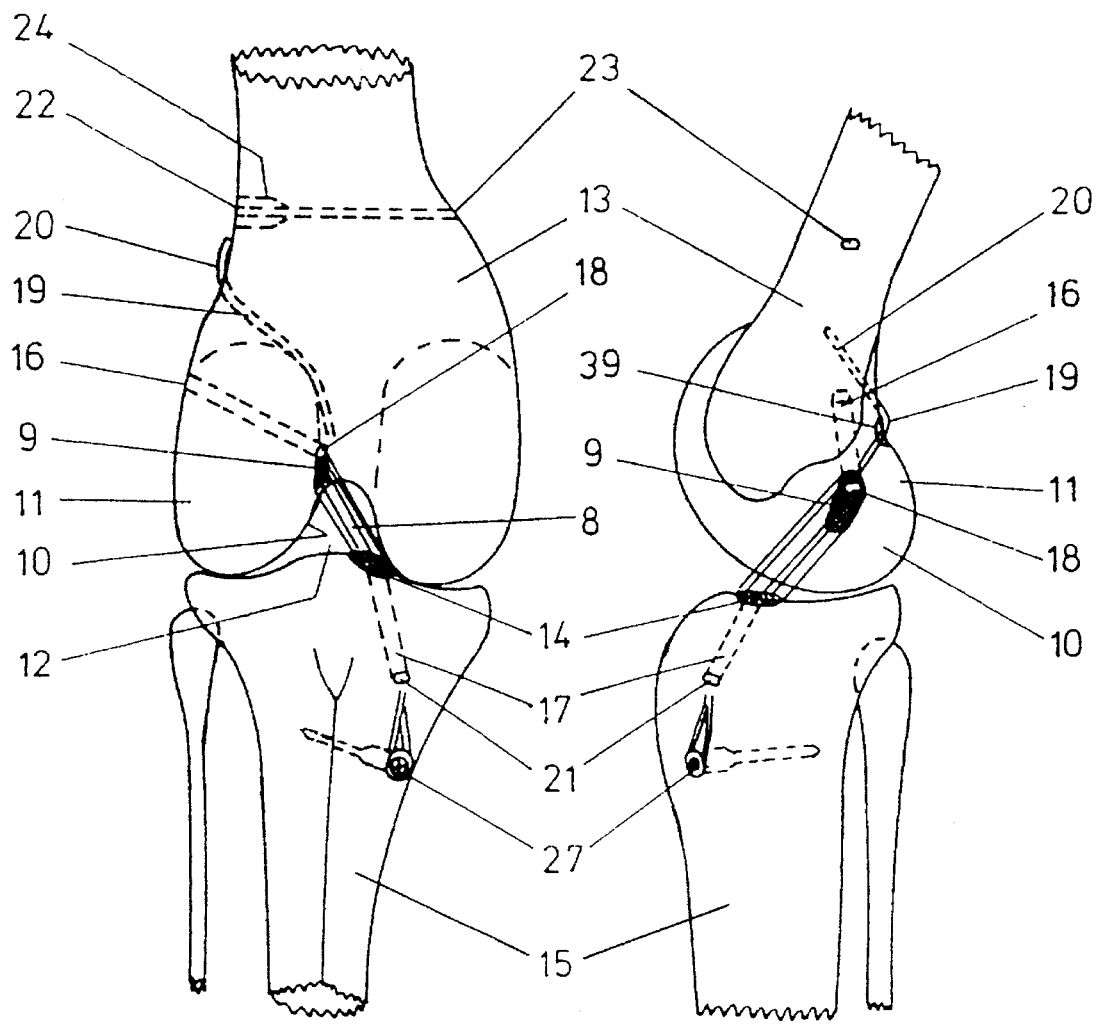
FIG. 2 shows a method of replacing the anterior cruciate ligament with an artificial ligament of the present invention.

In use, the ligament is placed across the knee joint on a pathway as close as possible to that of the natural ligament 8 (see FIG. 2). This originates from an area 9 on the medial face 10 of the lateral femoral condyle 11 which is situated posterialy in the intercondylar notch 12 of the femur 13. The ligament passes across the knee joint in an anterior and slightly medial direction, to its insertion site 14 on the superior surface of the tibia 15.

If the artificial ligament is to be in the same position, the obvious action is to drill holes 16, 17 through the femur and tibia respectively to the exterior surfaces, so that the implant can emerge from or insert into, the bones at the correct points. This procedure is sometimes followed for the insertion of these devices, but there is evidence that the implants are abraded where they emerge from the femoral bone hole 18 as the knee moves. This can be avoided by passing the implant across the surface of the intercondylar notch of the femur until it can be taken over the top of the lateral femoral condyle 19, to reach the lateral surface of the femur 20. This gives a very close approximation to the path of the natural ligament and is known as the "over the top" route.

The distal end of the implant is passed through a hole 17 drilled through the tibia between the insertion on the superior surface 14 and a point some 5 cm distal, on the antero-medial face 21. The fixation is accomplished by means of a metallic bone screw 5 passing through a metallic grommet 6. The loop 4 of fibres passes around the grommet and is held down by a flange 7 which is integral with the grommet, as shown in FIG. 1.

The grommet, two of which are used to fix the ligament across the knee joint, serves various purposes. It provides a smooth seating for the implant loop, and the flange 7 secures the loop against escape. The larger outer diameter of the grommets decreases the stress imposed on the bone, and the tapered end 29 expands the implant loop to tension it during insertion. The smooth seating 6 of the grommet is of a larger diameter than the shank of a bone screw, as well as being without sharp edged threads. Thus it will anchor the implant with lower stresses than if it were simply looped around the bone screw, decreasing the likelihood of failure at the anchorage point. The flange 7 gives greater security than the head of a bone screw, the latter 5 having a conical under surface. The edge of the flange 7 is kept thin and has a rounded shape to minimise soft tissue disruption, particularly if close beneath the skin. The grommet is countersunk (30) to completely accommodate the head of the bone screw 5 for the same reasons.

The large outer diameter of the grommet is important because it lowers the stress imposed on the bone during use. The bone is essentially a thin walled tube 2 containing weaker spongey bone. The artificial ligament will load the anchorage screw in a sideways direction, which will be resisted mainly by sideways reaction forces where the anchorage passes through the bone shell. A bone screw used alone will impose too high a compressive stress on the bone beneath its head. Loads in use will lead to a gradual cutting out by the screw, like a cheese wire. The grommet is intended to avoid this.

The implant will probably be set up with some tension by the surgeon, the anchorage hole being drilled accordingly. Thus the end of the loop will need to be expanded as the second anchorage device is driven home, hence the tapered end 29 on the grommet. The surface finish of the grommet is another important factor. A grommet with a smooth turned finish will not actually interlock with the bone, functioning solely against sideways forces. Incorporation of a fine pitch buttress thread form, or a series of circumferential grooves with a saw tooth form 31 on the cylindrical part of the outer surface, would increase interlocking of the grommet with the bone, giving the grommet an ability to resist forces tending to pull it out of the bone, rather than relying solely on the bone screw tip. Further enhancement could be obtained by the use of porous surfaces 32, to provide bone ingrowth interlocking on an intimate scale. This could be created by sintering on a layer of beads or kinked wires of the same material as the grommet. One possible problem here is that the implant fibres could snag on this type of surface during insertion, causing them to be dragged into the bone hole and damaged. This could be avoided by inserting the porous material between smooth surfaced ribs 33.

Figure 3:
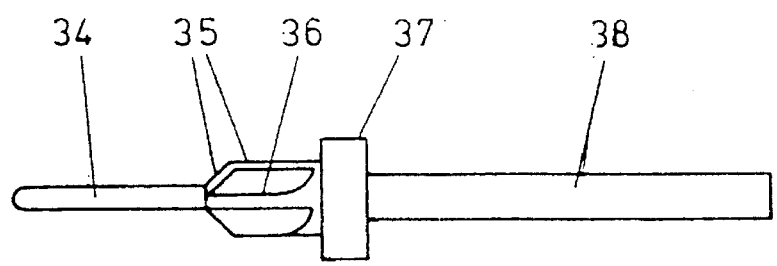
FIG. 3 shows a counterborer for use in the implantation of a ligament having looped ends.

When implanting the ligament, it is normal practise to fix the proximal end first. After threading the implant through the knee, over the femoral condyle and down the tibia, the approximate positions of the end loops are found. The proximal fixation hole starts on the lateral side of the femur 22, where a tapping drill hole is made for a bone screw. This is approximately 3 mm in diameter and passes right across the femur to emerge at the medial side 23. Unless the screw to be used is self-tapping, the drill hole is tapped with a screw thread at this stage. The entrance 24 to the drill hole is opened out to the size of the grommet 6, using a counterboring tool 25, such as that shown in FIG. 3 and described below.

The diameter of the bone is measured and a screw chosen which will just protrude from the far side 26. The screw 5 is passed through the grommet 6 and the loop 4 at the end of the implant passed around the grommet. The bone screw and grommet is then driven in so that the loop 4 is trapped against the bone surface. The implant is then pulled tight through the joint using the loop at the bottom end. The optimal position of the second screw is found, so that the joint is restored to normal stability, then it is inserted across the tibia using the same technique.

The counterborer 25 enlarges the tapping drill hole to the size of the grommet. It has a pilot rod 34 to follow the drill hole, then a section the same shape as the grommet 35 into which are machined cutting surfaces 36. A ring of larger diameter 37 acts as a depth stop. A shaft 38 is mounted in a drill chuck in use.

A drill guide, of which various types have been produced in the past, is used to ensure that the drill hole through the tibia emerges into the joint space correctly, through the ligament insertion. A hook rasp is also used—this creates a groove for the implant to lay in as it passes over the femoral condyle, deepening the angle between the condyle and the femoral shaft 39.

Presently, the tension in an artificial ligament, for example an artificial ACL, is usually achieved by guesswork, although it is vital to achieve the correct tension. If the ligament is too tight it will be predisposed to failure and will also inhibit joint motion. If it is too slack, the knee will be unstable.

A tensioning instrument according to the present invention may take various forms, as shown in FIGS. 4a to 4d and FIG. 5. In its simplest form, shown in FIG. 4a, the instrument is basically a hook on a handle. For use with ligaments having end loops, such as that of the present invention, the hook is shaped as a capstan 40 with the same waist diameter as the grommet 6, and is used to pull the end loop 4 of the implant down the tibia. The undersurface has a spike 41 which is hammered into the bone surface when the operator feels that it is in the correct place. The spike prevents the loop from moving and also marks the bone. The surgeon may then test the knee for stability and motion, either accepting the position or trying a new one. The drill holes can then be placed accurately, using the hole left by the spike. A range of capstans may be provided to suit different implant end loop sizes to enable the device to be used with other types of implants.

Figure 4A:
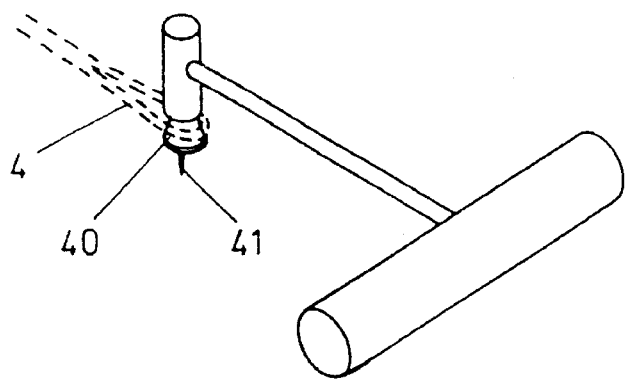
FIGS. 4a to 4d show various embodiments of a tensioning instrument according to the present invention.
Figure 4B:
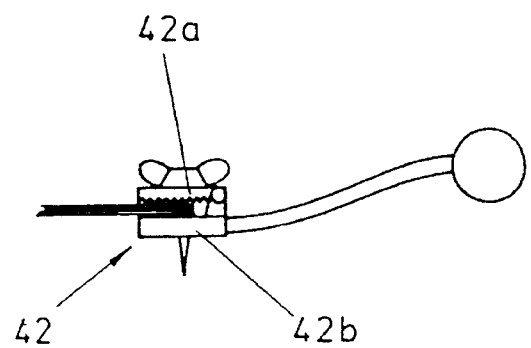

FIG. 4b shows an alternative device 42 for use with implants without end loops. In this device, two plates 42a and 42b are screwed together, gripping the ligament end between them, serrations being provided on one or both plates for this purpose.

Figure 4C:
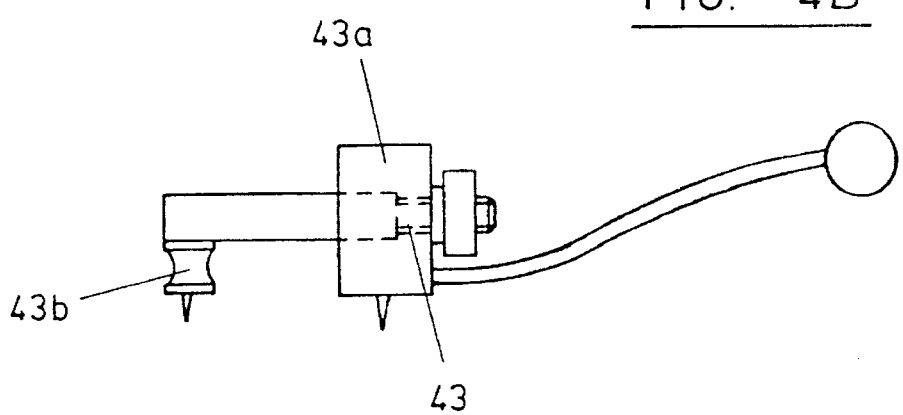

Since multiple attempts at marking the correct position would lead to confusion when choosing one of the spike holes for drilling, an improved version of implant tensioning tool could include an adjuster to enable the bone to be marked only when the desired tension has been achieved. FIG. 4c shows one such possible device, wherein the stationary datum 43a is impacted into the bone. The capstan 43b is moved relative to this datum until the desired tension is achieved, and the capstan spike is then hammered into the bone to provide the marker point.

Figure 4D:
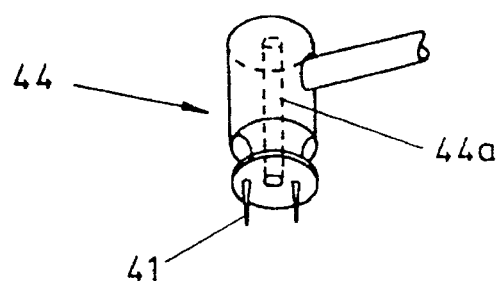

In FIG. 4d, the capstan is set up as a drill guide 44 to avoid having to move it after finding the correct spot, and the spikes 41 are set around the central hole 44a. This alternative may be employed in both types of tensioning device referred to above.

Figure 5:
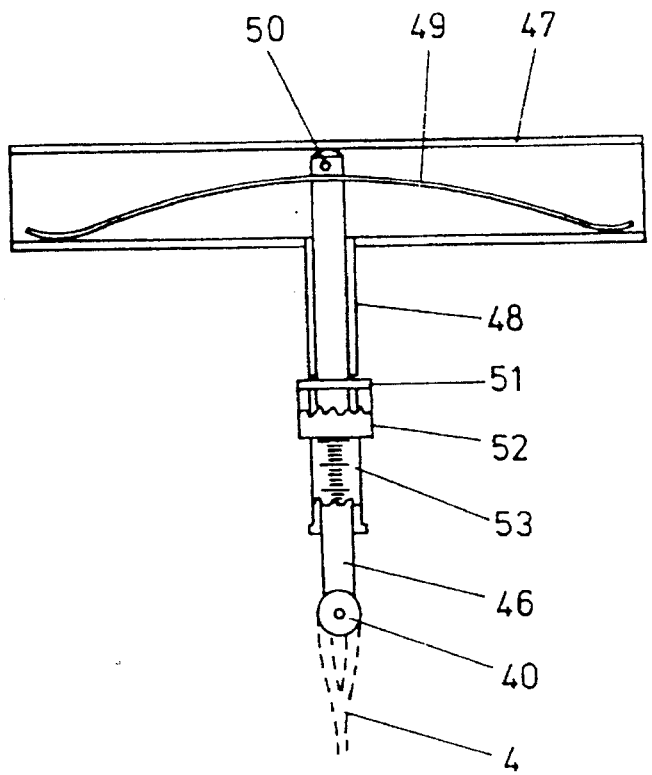
FIG. 5 shows an alternative tensioning instrument.

All of these variations depend on the surgeon's judgement of knee behaviour. An alternative, as shown in FIG. 5, would be to incorporate a force transducer into the tool 45, for example a spring balance in the handle, to show the tension in the implant as the knee is moved around by the surgeon. It may be that there is a particular tension that is correct with the knee at rest.

The device shown in FIG. 5 uses the implant loop 4 acting on a capstan 40 to pull a spindle 46 out of the handle 47 and guide tube 48 assembly, deforming a spring 49 which is acted on by a cross pin 50. A further cross pin 51 which is fixed in the spindle 46 slides along slots in the wall of the guide tube 48, moving a sliding ring 52 along the guide tube in response to the spring deflection, leaving the ring 52 to record on scale 53 the tension in the ligament as the knee is moved around. One disadvantage of the arrangement shown in FIG. 5 is that the highest tension recorded by the ring 52 will depend on the stiffness of the spring 49 in the handle 47, i.e. the instrument is not isometric. If the tensioning instrument were made so that it did not deflect appreciably (i.e. an isometric instrument) then the ligament would be stretched as the knee is moved in a manner which is a truer representation of the situation after the ligament has been anchored to the bone, and the peak tension recorded will most probably be much higher.

Figure 6:
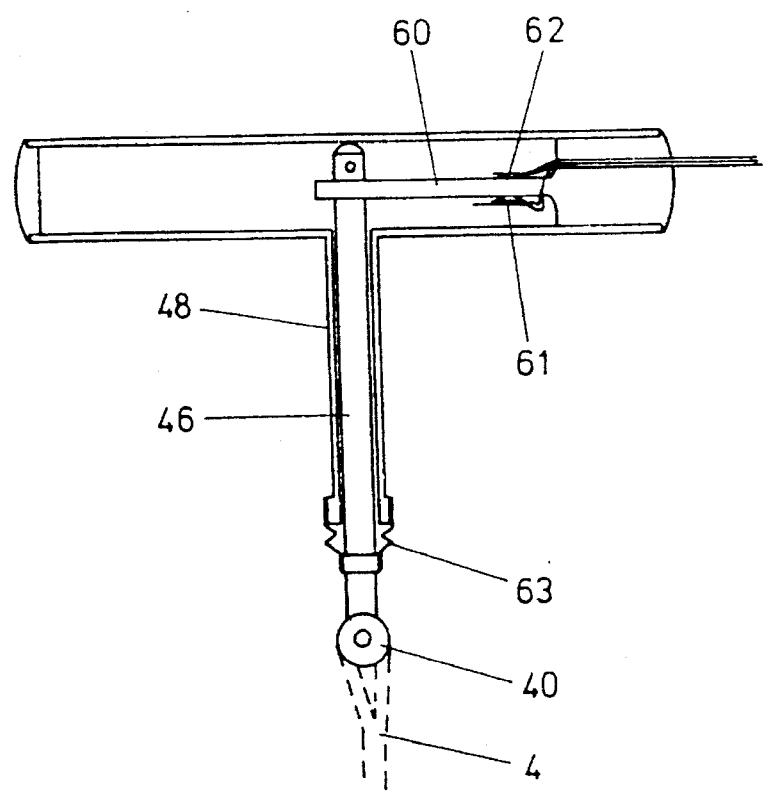
FIG. 6 shows a further alternative tensioning instrument.

Such an isometric instrument is shown in FIG. 6, in which a beam 60 deflects only very slightly under load and has attached on each side thereof strain gauges 61, 62 to sense the bending of the beam 60 and transmit the resulting electrical signal to an amplifier and read-out device (not shown). Instead of the sliding ring 52 as in FIG. 5, the space between the tube 48 and spindle 46 is merely sealed with a flexible seal 63. This arrangement could be made completely self-contained by increasing the bulk of the handle and incorporating into the handle a power pack, amplifier and read-out display e.g. a liquid crystal display, thus avoiding the necessity of having a mains unit and wires in the operating theatre.

I claim:

1. An artificial ligament for connecting across a skeletal joint, the ligament comprising a plurality of substantially parallel fibres which extend between (a) a first end for accommodating first fixation means by which the ligament can be secured to a first bone of the said joint, and (b) a second end for accommodating second fixation means by which the ligament can be secured across the joint to a second bone of the said joint; each of the fibres being formed from a yarn comprising a plurality of filaments of a biocompatible polymeric material that are slightly twisted together so as to form the yarn, the filaments being unconnected and continuously exposed along substantially their entire surfaces between the first and second ends to facilitate parallel uninhibited ingrowth of collagenous tissue into the structure of the yarn fibres between and along individual ones of the filaments and the fibres resulting in encapsulation of the filaments to form a composite load bearing structure of the filaments and the ingrown collagenous tissue which extends continuously between the first and second bones of the joint, without strangulation of tissue that has ingrown into spaces between the filaments.

2. An artificial ligament according to claim 1 in which the ligament has a loop at each end formed by binding the fibres together.

3. An artificial ligament according to claim 1 in which the fibres are polyethylene terephthalate fibres.

4. An artificial ligament according to claim 1 in which the diameter of each filament is 15 microns.

5. An artificial ligament according to claim 1 in which the diameter of each filament is from 5 to 25 microns.

* * * * *